US010137319B2

(12) United States Patent
Carr et al.

(10) Patent No.: US 10,137,319 B2
(45) Date of Patent: Nov. 27, 2018

(54) CARRYING SYSTEM FOR BREATHING APPARATUS

(75) Inventors: Robert Carr, Skelmersdale (GB); Steven Thurgood, Skelmersdale (GB); Barry Lewin, Skelmersdale (GB); Tony Pickett, Skelmersdale (GB)

(73) Assignee: SCOTT HEALTH & SAFETY LTD., Skelmersdale, Lancashire (GB)

(*) Notice: Subject to any disclaimer, the term of this patent is extended or adjusted under 35 U.S.C. 154(b) by 610 days.

(21) Appl. No.: 12/936,177

(22) PCT Filed: Apr. 8, 2009

(86) PCT No.: PCT/GB2009/050346
§ 371 (c)(1), (2), (4) Date: Nov. 11, 2010

(87) PCT Pub. No.: WO2009/125223
PCT Pub. Date: Oct. 15, 2009

(65) Prior Publication Data

US 2011/0048421 A1 Mar. 3, 2011

(30) Foreign Application Priority Data

Apr. 8, 2008 (GB) .................................. 0806359.6

(51) Int. Cl.
*A61M 16/00* (2006.01)
*A62B 25/00* (2006.01)
(Continued)

(52) U.S. Cl.
CPC .................. *A62B 9/04* (2013.01); *A45F 3/10* (2013.01); *A62B 25/00* (2013.01); *B63C 11/02* (2013.01);
(Continued)

(58) Field of Classification Search
CPC .............. A61M 16/06; A61M 16/0627; A61M 16/10–16/1015; A62B 7/00–7/14;
(Continued)

(56) References Cited

U.S. PATENT DOCUMENTS

| | | | | |
|---|---|---|---|---|
| 3,957,183 A * | 5/1976 | Gadberry | ...................... | 224/628 |
| 4,250,876 A * | 2/1981 | Kranz | ...................... | 128/202.22 |

(Continued)

FOREIGN PATENT DOCUMENTS

| | | |
|---|---|---|
| DE | 10228388 | 1/2004 |
| EP | 0747095 | 12/1996 |
| GB | 1537268 | 12/1978 |
| GB | 2400014 | 10/2004 |
| GB | 2400014 A * | 10/2004 |

*Primary Examiner* — Gregory Anderson
*Assistant Examiner* — Ned T Heffner
(74) *Attorney, Agent, or Firm* — Dean D. Small; The Small Patent Law Group, LLC

(57) ABSTRACT

A carrying system is provided for use with breathing apparatus. The carrying system includes a backplate and a plurality of straps adapted to hold the backplate on the back of a user when the carrying system is worn. The backplate includes at least one plate of a plastics material. The at least one plate having a predetermined shape and the at least one plate being adapted to provide impact protection to a user during use by at least partially absorbing and/or dispersing impact forces, and to deform resiliency in response to external forces imposed by bending and/or twisting of a user during use and return substantially to its predetermined shape when not subjected to an external force.

23 Claims, 9 Drawing Sheets

(51) Int. Cl.

| | |
|---|---|
| ***A62B 9/04*** | (2006.01) |
| ***A45F 3/10*** | (2006.01) |
| ***B63C 11/02*** | (2006.01) |
| *A45F 3/04* | (2006.01) |

(52) U.S. Cl.
CPC ... *A45F 2003/045* (2013.01); *B63C 2011/026* (2013.01)

(58) Field of Classification Search
CPC ......... A62B 9/003–9/06; A62B 17/003; A62B 17/08; A62B 25/00–25/005; B63C 11/00–11/04; B63C 2011/026
USPC ............ 128/205.22, 202.27, 204.18, 200.24, 128/200.27, 200.28; 24/311
See application file for complete search history.

(56) References Cited

U.S. PATENT DOCUMENTS

| | | | | |
|---|---|---|---|---|
| 4,604,772 | A * | 8/1986 | Arff | 24/68 R |
| 4,979,659 | A * | 12/1990 | Boyd | 224/603 |
| 5,054,170 | A * | 10/1991 | Otrusina | 24/580.11 |
| 5,564,612 | A | 10/1996 | Gregory | |
| 5,626,439 | A * | 5/1997 | Rowlands | 405/186 |
| 5,730,347 | A * | 3/1998 | Finot | 224/631 |
| 5,954,250 | A * | 9/1999 | Hall et al. | 224/262 |
| 5,954,253 | A | 9/1999 | Swetish | |
| 6,401,715 | B1 | 6/2002 | Leuthe | |
| 2002/0162871 | A1* | 11/2002 | Vigny | A45F 3/04 224/628 |
| 2003/0005933 | A1* | 1/2003 | Izuchukwu | 128/205.22 |
| 2007/0090137 | A1* | 4/2007 | Kim | 224/153 |

* cited by examiner

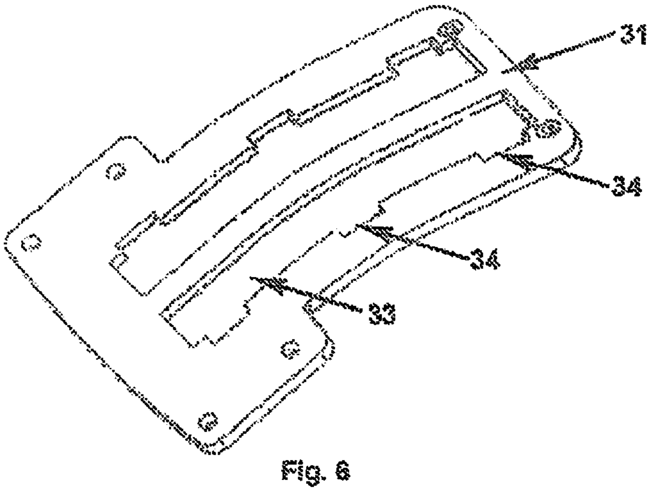
Fig. 6
Fig. 7a
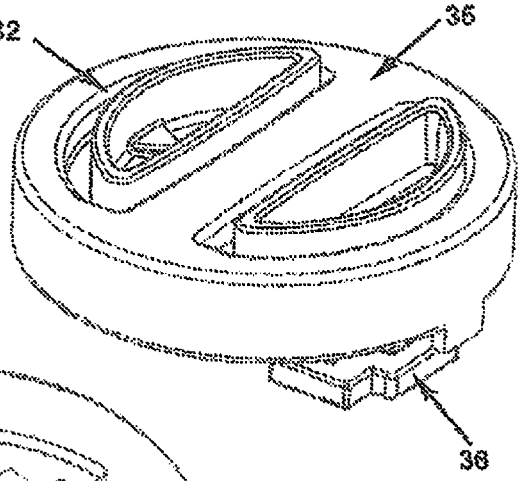
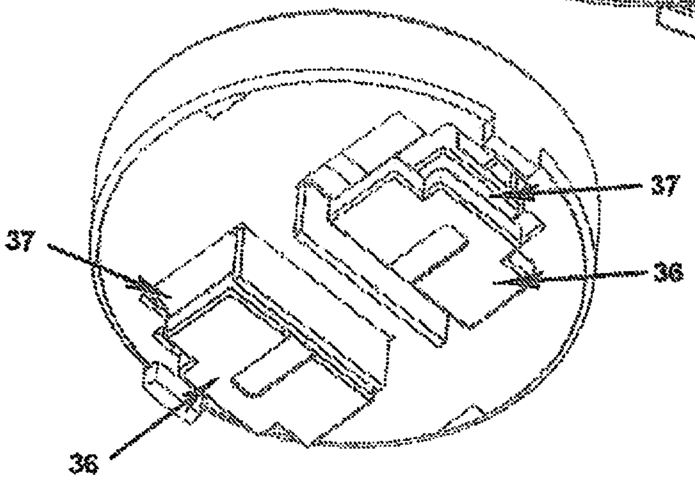
Fig. 7b

CARRYING SYSTEM FOR BREATHING APPARATUS

CROSS REFERENCE TO RELATED APPLICATIONS

This application claims priority to and benefit of the filing date of PCT Application No. PCT/GB2009/050346, filed Apr. 8, 2009, and Great Britain Patent application No. GB 0806359.6, filed Apr. 8, 2008, which are each hereby incorporated by reference in their entirety.

BACKGROUND OF THE INVENTION

The subject matter described and/or illustrated herein relates to a carrying system adapted for use with breathing apparatus. Particularly, but not exclusively, the subject matter described and/or illustrated herein is concerned with harnesses for carrying one or more air cylinders for use in emergency situations by people such as fire-fighters and others who may be exposed to contaminated and hostile environments.

Often fire-fighters are required to work in areas where the air cannot be inhaled for example because the air includes harmful gases. In such contaminated environments fire-fighters use breathing apparatus that comprises an air cylinder, a mask and supply lines connecting the air cylinder to the mask for delivering a protected breathable supply of air. However, the air in the cylinder is usually pressurised and as a result the air cylinder is heavy and cumbersome for fire-fighters to carry. For this reason, carrying systems have been devised to assist fire-fighters and others in carrying breathing apparatus. In general, such carrying systems consist of a harness to which the air cylinder is attached which includes one or more shoulder straps and a belt strap which are worn around the body so that the harness and hence the air cylinder are strapped to the body leaving the fire-fighter's hands and arms free.

In GB 2302009 a conventional harness for use with breathing apparatus is described. The harness includes a backplate which is flexible into and out of the plane of the wearer's back and a pivotal connection between the backplate and the belt for permitting sideways movement. The pivotal connection is also adapted to freely move in a longitudinal slot in the backplate so that the length of the harness adjusts during use. However, little information is provided as to how air is fed from the air cylinders to the mask of the breathing apparatus.

A different harness is described in GB 2400014 which includes at least one flexible shoulder panel and a flexible mounting plate to which an air cylinder is attached. The shoulder panel is made of a compression moulded EVA foam which, whilst being flexible, is stiffened so that the shoulder panel retains its operational configuration even when not being worn.

In EP 1253967 an alternative carrying system is described in which a rigid backplate is divided in two to enable the longitudinal length of the carrying system to be adjusted to accommodate the different back lengths of different wearers. The air supply lines follow a path between the two halves of the backplate and therefore are not easily accessible.

BRIEF DESCRIPTION OF THE INVENTION

The subject matter described and/or illustrated herein seeks to address problems encountered with conventional carrying systems, such as those described above, and seeks to provide an improved carrying system.

An object of the subject matter described and/or illustrated herein is to provide a carrying system which, when worn, is comfortable for a user and does not significantly impede the movements of the user.

A further object of the subject matter described and/or illustrated herein is to provide a carrying system which is capable of flexing in one or more directions.

A still further object of the subject matter described and/or illustrated herein is the provision of a carrying system which offers reliable protection to the upper body of a user.

A yet further object of the subject matter described and/or illustrated herein is to provide a carrying system which includes high quality padding to further improve user comfort.

A yet further object of the subject matter described and/or illustrated herein is to provide a carrying system which ensures correct setting of the centre of gravity for any load carried by the carrying system.

A yet further object of the subject matter described and/or illustrated herein is to provide a carrying system which permits adjustment of the carrying system to accommodate different sizes of user whilst maintaining proper transference of the load to the user irrespective of the size of the user.

A yet further object of the subject matter described and/or illustrated herein is to provide a carrying system which permits simple and quick attachment and removal of breathing apparatus to and from the carrying system.

A yet further object of the subject matter described and/or illustrated herein is to provide a carrying system which can be washed in a conventional washing machine.

A yet further object of the subject matter described and/or illustrated herein is to provide a carrying system which ensures that an air cylinder mounted on the carrying system is reliably held in position and that the air cylinder is not inadvertently or unintentionally loosened during use.

The subject matter described and/or illustrated herein therefore provides in a first aspect a carrying system for use with breathing apparatus including a backplate and a plurality of straps adapted to hold the backplate on the back of a user when the carrying system is worn, the backplate including at least one plate of a plastics material, the at least one plate having a predetermined shape and the at least one plate being adapted to: provide impact protection to a user during use by at least partially absorbing and/or dispersing impact forces, and to deform resiliency in response to external forces imposed by bending and/or twisting of a user during use and return substantially to its predetermined shape when not subjected to an external force.

In some embodiments, the at least one plate is adapted to deform torsionally in response to a twisting movement of the user's back during use. Also, in some embodiments, the at least one plate is adapted to deform substantially wholly elastically whereby the movement of a user when wearing the carrying system is substantially unimpeded by the backplate.

In some embodiments, the backplate comprises a planar element consisting of a single plate, the predetermined shape of the single plate being contoured to follow at least approximately the natural contours of a human back in at least one dimensional aspect.

In some embodiments, the backplate includes an upper guard region adapted to protect at least part of the cervical region and/or the upper thoracic region of a user; and one or more tensioning straps attached to the upper guard region, the upper guard region being adapted to flex relative to the remainder of the backplate so as to substantially overlie at least some of the cervical area and/or the upper thoracic area of the user, when tension is applied to the one or more tensioning straps.

The backplate may additionally include one or more areas of thermoformed padding which may be to follow at least approximately the natural contours of a human back in at least one dimensional aspect.

In some embodiments, the straps include a waist strap and the backplate and waist strap include interengaging means for relative slidable engagement, the interengaging means defining a plurality of engagement positions of the waist strap relative to the backplate, each engagement position including means for locking the engagement position whereby in each one of the plurality of engagement positions the weight of any load carried by the carrying system when worn is substantially transferred to the waist strap. Also, the straps may include a waist strap which is pivotally attached to the backplate to permit relative pivotal movement between the waist strap and the backplate.

In a separate aspect of various embodiments of the present invention a carrying system is provided for use with breathing apparatus, the carrying system including a backplate and a plurality of straps adapted to hold the backplate on the back of a user when the carrying system is worn, the backplate including a first attachment member mounted on the backplate which first attachment member is adapted to releasably attach to a connecting part of the breathing apparatus which, in use, connects an air cylinder to one or more air supply hoses, wherein the connecting part of the breathing apparatus is manually releasably attachable to and from said first attachment member by a user without the use of a tool.

In some embodiments, a mounting adapted for releaseable inter-engagement with the first attachment member is provided and is further adapted for attachment to the connecting part of the breathing apparatus. Also, the first attachment member may comprise an aperture adapted to receive the mounting and the aperture being shaped to permit relative rotation of the mounting within the aperture between unlocked and locked states.

In some embodiments, the backplate further includes a second attachment member mounted on the backplate, the second attachment member comprising a cylinder supporting surface and an adjustable flexible strap for encircling the air cylinder of the breathing apparatus, the cylinder supporting surface and the flexible strap forming a continuous loop the diameter of which is manually adjustable to conform to the diameter of an air cylinder.

Optionally, the flexible strap includes a strap lock for locking the strap at a chosen strap loop diameter, the strap lock comprising a pair of pivotally connected strap holding members wherein the pivotal connection of the pair of strap holding members includes a locking mechanism for locking the relative position of the pair of strap holding members and the locking mechanism further includes a pair of opposing release buttons for manual release of the locking mechanism.

The second attachment may further include one or more hose channels for releasably engaging one or more air supply hoses of the breathing apparatus, the hose channels being adapted to provide an interference fit for the air supply hoses, whereby a user may engage and disengage the one or more air supply hoses to and from the hose channels without the use of a tool. Also, in some embodiments, the first and second attachment members are separated by a distance corresponding to over half the length of the air cylinder of the breathing apparatus.

With the aspects of the various embodiments of the present invention described above an improved carrying system is provided for use, for example, by fire fighters which greatly increases comfort, reduces wearer fatigue and which offers a significant improvement in terms of wearer safety. In particular, with various embodiments of the present invention a carrying system is provided which, when worn, does not significantly impede the movements of the user. Also, the carrying system may be capable of flexing in one or more directions. Furthermore, the carrying system offers reliable protection to the upper body of a user and may include high quality padding to further improve user comfort.

Also, in some embodiments of the present invention the carrying system is adapted to ensure correct setting of the centre of gravity for any load carried by the carrying system and optionally the carrying system may permit adjustment to accommodate different sizes of user whilst maintaining proper transference of the load to the user irrespective of the size of the user.

Various embodiments of the present invention separately provide a carrying system which permits simple and quick attachment and removal of breathing apparatus to and from the carrying system. This, in turn, makes the carrying system suitable for washing in a conventional washing machine. Also, optionally the carrying system is adapted to ensure that an air cylinder mounted on the carrying system is reliably held in position and that the air cylinder is not inadvertently or unintentionally loosened during use.

BRIEF DESCRIPTION OF THE DRAWINGS

Embodiments of the present invention will now be described by way of example only with reference to the accompanying drawings, in which:

FIG. 6 illustrates a waist strap position adjustment guide provided with the carrying system in accordance with an embodiment of the present invention; and FIGS. 7*a* and 7*b* illustrate a waist strap adjustment follower for use with the adjustment guide of FIG. 6;

DETAILED DESCRIPTION OF THE INVENTION

Figure 1:
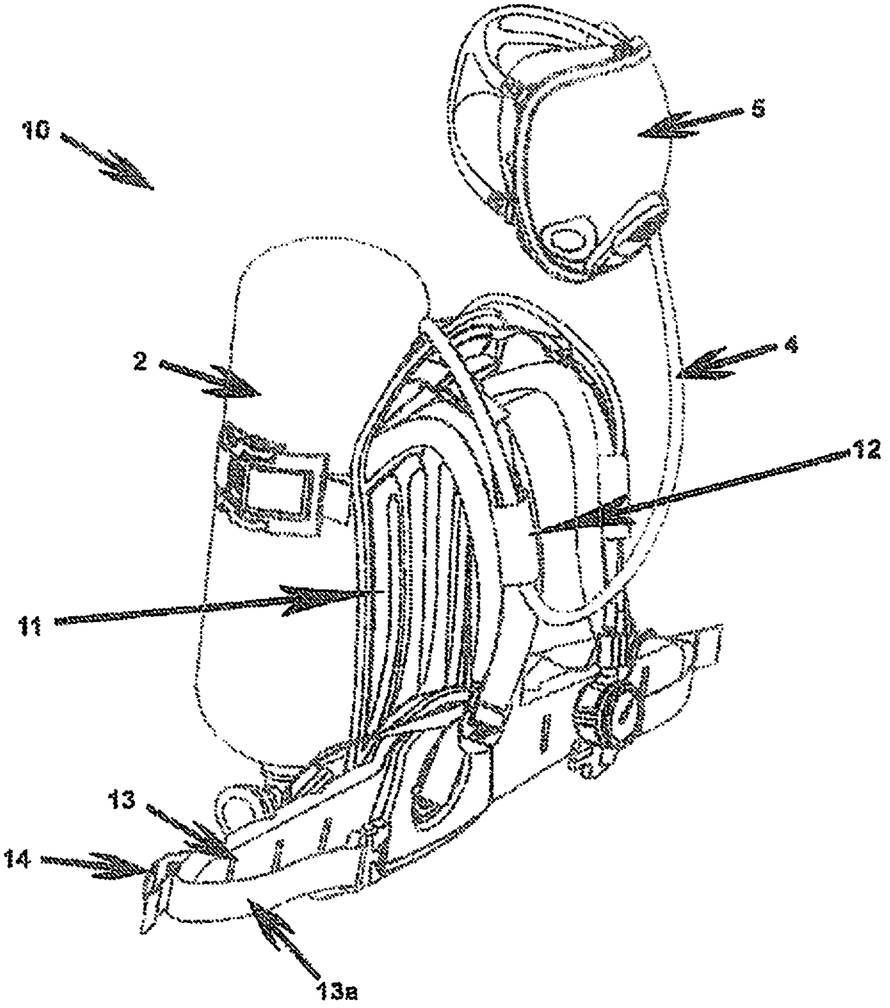
FIG. 1 is a photographic image of a carrying system in accordance with an embodiment of the present invention with breathing apparatus attached.

As shown in FIG. 1 the carrying system 10 generally comprises a backplate 11 onto which at least one air cylinder 2 may be mounted; a pair of shoulder straps 12 which are attached at their upper ends 12*a* to the backplate 11; and a waist strap 13 attached to a lower region of the backplate 11. The waist strap 13 extends away from the backplate in opposing directions and is attached to the lower ends 12*b* of the shoulder straps 12. The carrying system 10 is worn by positioning the backplate 11 over the wearer's back with the outer side of the backplate 11 facing away from the wearer. The waist strap 13 is aligned with the wearer's lumbar region and encircles the wearer's waist with the two free ends 13*a* of the waist strap 13 engaging with each other at the front of the wearer whilst the shoulder straps 12 are positioned over the wearer's shoulders. Thus, the weight of the carrying system and anything carried by the carrying system, such as air cylinders, is supported by the backplate which transmits the majority of the load to the waist strap 13 and thus to the wearer's hips, leaving the wearer's hands and arms free. The shoulder straps 12 ensure that the carrying system is properly aligned and that the load mounted on the backplate 11 is held close to the wearer's body and with the centre of gravity of the breathing system in the correct position relative to the wearer's back.

Figure 3:
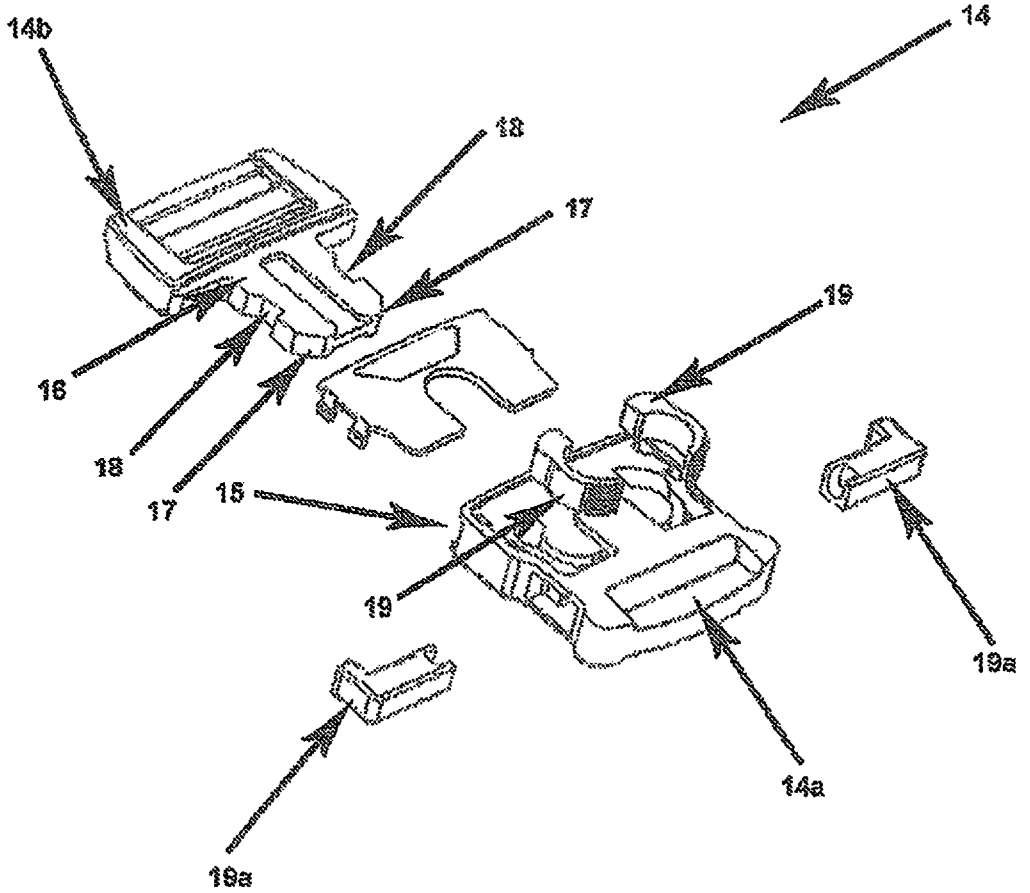
FIG. 3 is an exploded illustration of a waist strap buckle.

The two ends 13*a* of the waist strap 13 may be secured to each other by tying or by using any conventional belt-type connector. Optionally, the free ends 13*a* of the waist strap 13 are provided with first and second interengaging portions 14*a*, 14*b* of a buckle 14 such as a cam locking buckle which may be more clearly seen in FIG. 3. The first and second interengaging portions 14*a*, 14*b* of the buckle comprise respectively a receiving slot 15 and a tongue 16 for insertion into the receiving slot 15. The tongue 16 has along opposing side edges cam surfaces 17 and shoulders 18, remote from the free end of the tongue 16. When the tongue 16 on the second buckle portion 14*b* is inserted into the receiving slot 15 of the first buckle portion 14*a*, the cam surfaces 17 on the tongue 17 engage with respective lugs 19 biased so as to project into the receiving slot 15. As the tongue 16 is inserted further into the receiving slot 15, the interaction of the cam surfaces 17 on the lugs 19 causes the lugs 19 to increase their separation by acting against the biasing force holding the lugs in position within the receiving slot 15. Once the cam surfaces 17 pass beyond the lugs 19, the biasing force acting on the lugs 19 causes the lugs 19 to engage with the respective shoulders 18 on the tongue 16 thereby locking the two buckle portions together.

The buckle 14 is released by the actuation of two opposing release buttons 19*a* provided on the first buckle portion 14*a*. The release buttons 19*a* are mounted for slidable movement of the buttons into the buckle portion 14*a*. Each one of the release buttons 19*a* engages with a respective one of the two lugs 19 by means of inter-engaging teeth. When the buckle 14 is to be unlocked, both buttons 19 are depressed simultaneously into the buckle portion 14*a*. This movement of the release buttons 19*a* causes, in turn, the lugs 19 to move against the biasing force acting on the lugs to release the lugs 19 from the shoulders 18 on the tongue 16. The tongue 16 can then be removed from the receiving slot 15. By providing two opposing release buttons 19*a* on the buckle, the risk of the buckle being released accidentally is significantly reduced because a compressive force applied simultaneously to both side edges of the buckle is, in practice, unlikely to occur accidentally.

Either on the first and second buckle portions or separately from the buckle 14, one or both parts of the waist strap 13 may include parachute-type strap adjusters 13*b*. Each strap adjuster 13*b* has a strap slot which is divided by a cross bar and is arranged to permits free movement of the strap through the strap slot in a shortening direction but to restrict movement of the strap through the strap slot in a lengthening direction, unless intentionally released. This enables the length of each end of the waist strap 13 to be quickly and easily adjusted to ensure the waist strap fits snugly around a wearer's waist. In its simplest form the cross bar may be slidable within the slot in a direction parallel to the strap length. Optionally, the cross bar, is adapted so that it interacts with the edges of the strap slot to engage with and hold the strap extending through the strap slot.

In some embodiments, similar parachute-type strap length adjustors 20 are provided on each of the shoulder straps intermediate its two ends 12*a*, 12*b*. This enables the length of the each of the shoulder straps to be quickly and easily adjusted whilst each end 12*a*, 12*b* of the shoulder strap 12 remains attached to the backplate 11 and the waist strap 13 respectively.

The backplate 11 of the carrying system may have one or more supporting plates. In the accompanying figures the backplate comprises a single planar element in the form of a single plate 11*a* which is shaped so as to be wider at each end region than at the middle and which has a length approximately equal to or greater than the length of a conventional air cylinder. The thickness of the backplate 11, approximately 10 mm, is much less than its width and its length. Also the plate forming the backplate 11 is contoured such that the plate approximately follows the curvature and contours of a human back in at least one and optionally two dimensions. Thus, all points on either the outer or inner surfaces of the backplate 11 do not lie in a common plane. As may be more clearly seen in FIGS. 10 and 11, the outer surface of a lower section of the backplate 11 lies approximately in a plane at an acute angle to the plane of a mid-section of the backplate 11 whereas an upper section of the backplate extends at an obtuse angle to the plane of the mid-section. The edge of the backplate 11 is continuous and is smoothly curved, and does not include any discontinuities which might catch on obstructions or the air supply hoses of the breathing apparatus.

The plate 11*a* is formed of a plastics material which is strong and lightweight. The plate 11 is sufficiently hard to absorb and/or disperse impact forces, for example the impact force of an air cylinder striking the backplate. Thus the plate 11*a* provides impact protection to the back of a wearer, generally absorbing and spreading the force of an impact over a significantly larger area than the initial point of impact. However, the plate 11*a* is also resilient and thus is capable of deforming in response to twisting and/or bending movements by the wearer, thereafter substantially returning to its original predetermined contoured shape. Thus, deformation of the plate 11*a* is substantially wholly elastic and with not or negligible plastic deformation. The backplate 11 is capable of flexing towards and away from the back of the wearer, i.e. fore- and aft of the wearer's back, and is also capable of deforming torsionally in which one of the long edges of the plate 11*a* flexes relative to the remainder of the plate. Such torsional flexure is likely to arise when a wearer twists his upper body whilst wearing the carrying system. The carrying system 10, excluding all breathing apparatus, has a weight in the range of 1.5 to 4 kg and, in some embodiments, 2.5 to 3 kg. These resilient characteristics of the plate 11*a* ensures that a wearer's movements are substantially unimpeded by the backplate 11 when the carrying system is worn.

Particularly when used by the fire services, the backplate 11 is covered in a flame retardant material such as treated nylon or Proban™ treated cotton. In some embodiments, the plate 11*a* is sandwiched between two layers of the flame retardant material which are bound together along their edges using flame retardant binding tape. The flame retardant covering material is washable and with the pneumatics and all air supply lines removed (see below) the carrying system described herein is particularly adapted to permit washing in a conventional washing machine.

Figure 4:
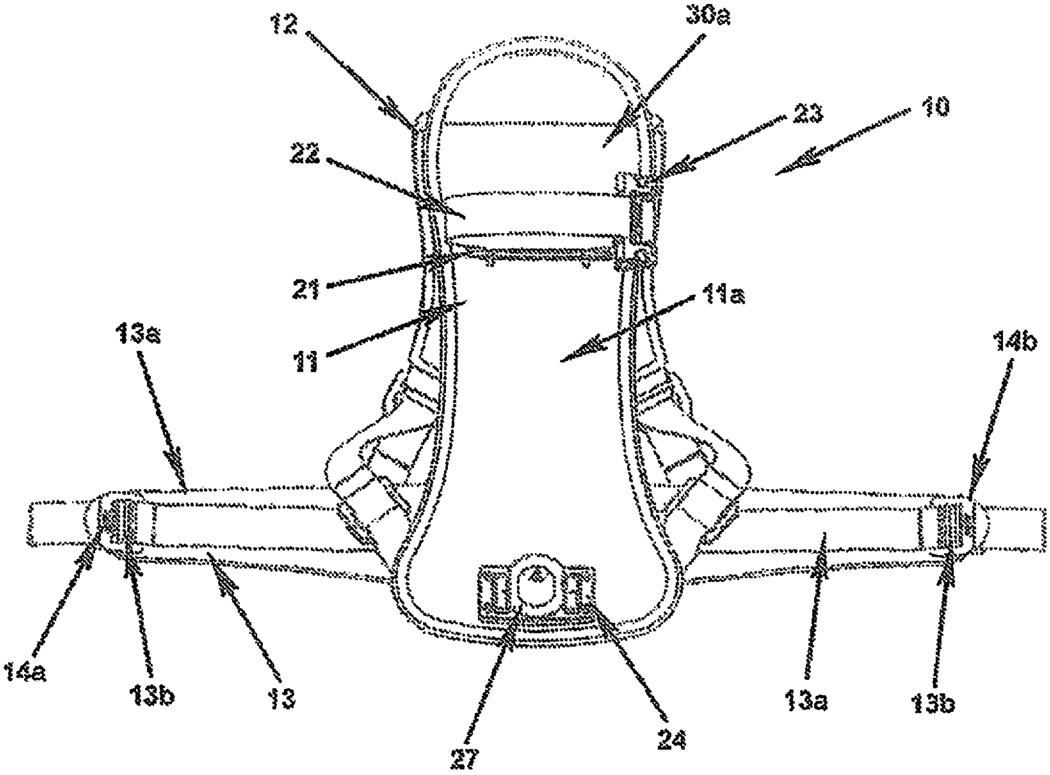
FIG. 4 is a further diagrammatic illustration of the carrying system of FIG. 1 looking towards the outer side of the carrying system, opposite to the side illustrated in FIG. 2.
Figure 5:
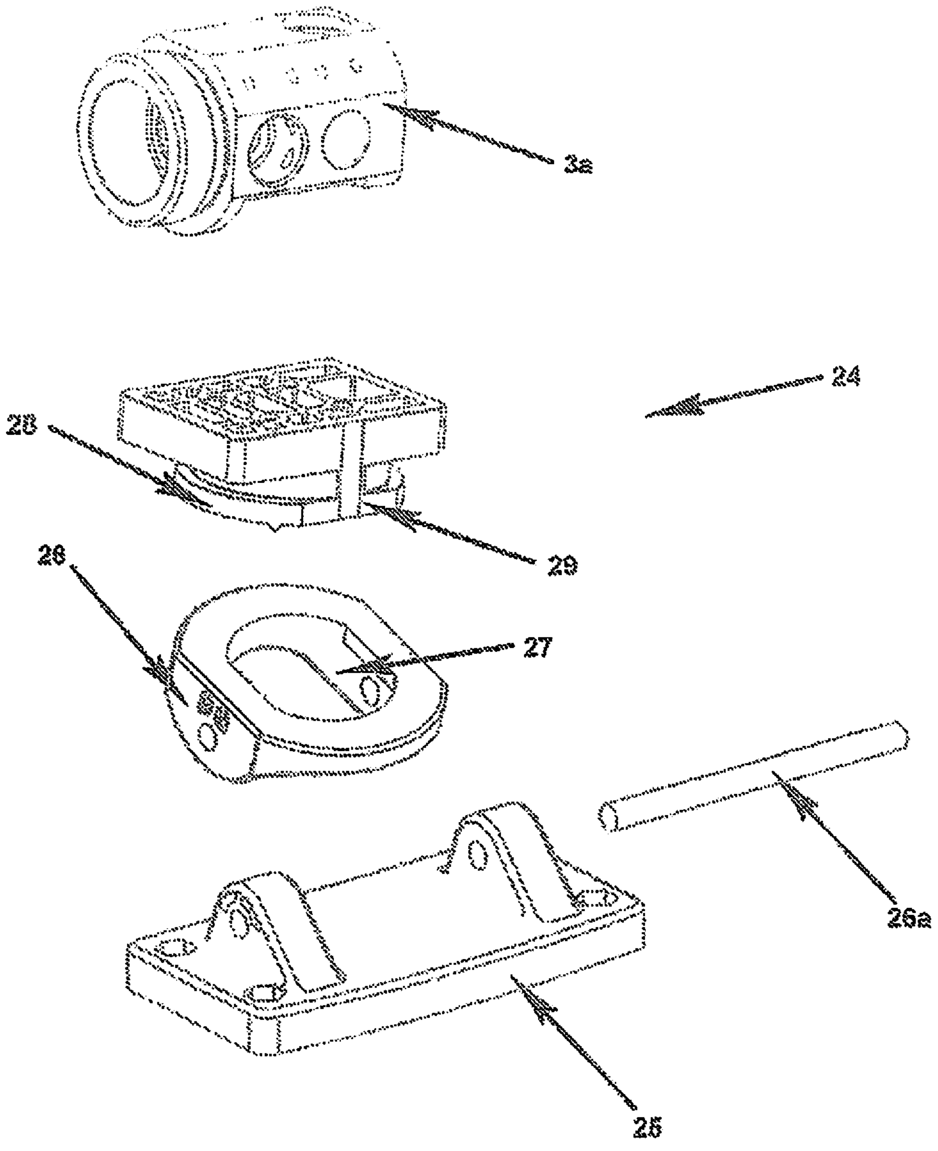
FIG. 5 is a detailed illustration of the reducer bracket of the carrying system in accordance with an embodiment of the present invention.

As shown in FIG. 4, a first cylinder attachment member is fixedly mounted close to the bottom edge of the backplate 11 and is in the form of a pneumatics mounting 24. The bracket 24 provides an attachment point for the demand valve 3 of an air cylinder 2 thereby enabling the air outlet of the cylinder 2 to be supported on the backplate 11 via the demand valve 3 and the mounting 24.

The pneumatics mounting 24 includes a base 25 fixed to the backplate 11 and a bracket 26 which is pivotally attached 26*a* to the base 25. The bracket 26 includes an aperture 27 which is shaped to receive a locking element 28 which is, in turn, intended for attachment to the connecting part 3*a* of the breathing apparatus which connects the air cylinder to the demand valve 3 and the pressure gauge of a conventional air supply apparatus i.e. the connecting part may consist of a pillar valve and a regulator. The locking element 28 and the aperture 27 are shaped so as to permit inter-engagement in one or more predetermined relative orientations. Additionally, the locking element 28 includes a shoulder 29 which is adapted to engage one of the edges of the aperture 27. In use, the locking element 28 is orientated for insertion into the aperture 27 in the bracket 26. Once inserted, the locking element 28 is then rotated, for example through 90°, so that the shoulder 29 on the locking element 28 engages with an edge of the aperture 27. In some embodiments, the interaction of the shoulder 29 with the edge of the aperture 27 includes an additional resilient locking mechanism (not shown) in order to maintain the relative rotational position of the locking element 28 in the aperture 27. In any event, when the carrying system is in use and an air cylinder is mounted on the backplate 11 and supplying air to a mask, the pressure of air flowing from the cylinder 2 via the pneumatics connecting part 3*a* provides an additional force on the attachment member 24 to maintain it in a locked position. To disengage the pneumatics connecting part 3*a*, the locking element 28 is rotated manually back to a position where it is free to be removed from the aperture 27. Thus, no tools are required to engage and disengage the pneumatics connecting part from the backplate 11.

As may be more clearly seen in FIG. 4, the carrying system 10 includes a second attachment member in the form of a cylinder cradle 21 provided on the outer surface of the backplate 11. In some embodiments, the cylinder cradle 21 is shaped to receive and accommodate the curvature of a conventional air cylinder 2 and, in some embodiments, the cradle 21 includes a removable insert (not shown) which enables the cradle 21 to accommodate different cylinder curvatures and/or two cylinders 2 in parallel instead of a single cylinder.

The cylinder cradle 21 additionally includes cylinder holding means 22 for holding one or more air cylinders 2 in position against the cylinder cradle 21. The cylinder holding means 22 is optionally a flexible strap which is adjustable in length. By providing a flexible strap 22 attached to the cylinder cradle 21, the carrying system 10 is capable of being used with a range of different air cylinder shapes and sizes and of being used with either one or two cylinders in parallel.

Figure 8:
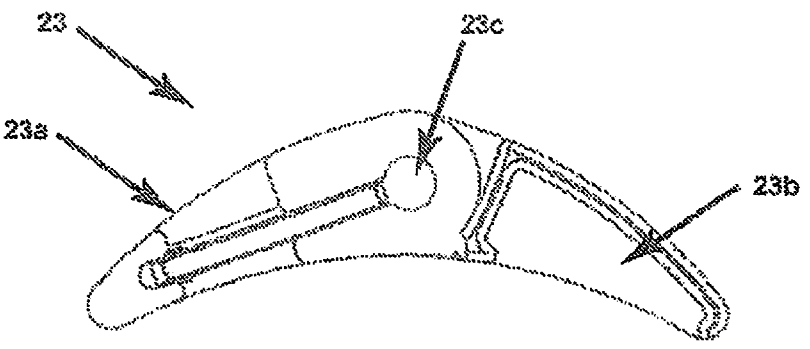
FIG. 8 is a side plan view of a cylinder strap adjuster.
Figure 9:
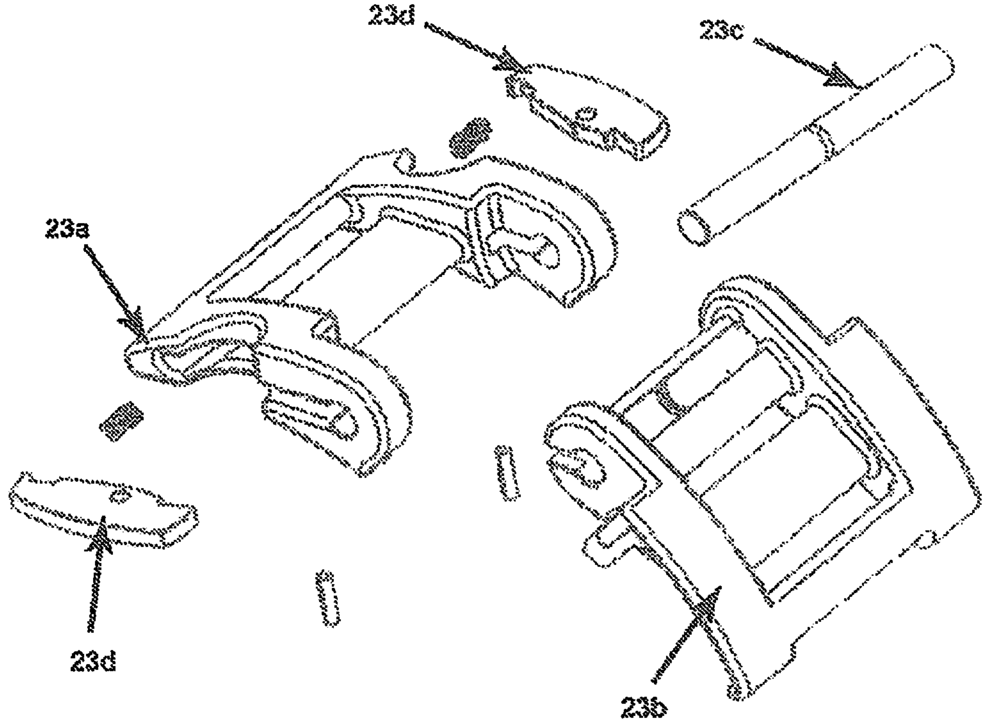
FIG. 9 is an exploded illustration of the cylinder strap adjuster of FIG. 8.

In some embodiments, the cylinder strap 22 is in the form of a continuous loop into which the air cylinder 2 is inserted and which is then tightened around the air cylinder. As shown in FIGS. 8 and 9, a cylinder strap adjuster 23, which is used to tighten the continuous loop, has first and second strap engagements 23*a*, 23*b* that are pivotally attached 23*c* to each other. One end of the cylinder strap 22 is attached to the end of the first portion 23*a* of the adjuster remote from the pivotal attachment 23*c* and similarly the other end of the cylinder strap is attached to the end of the second portion 23*b* of the adjuster also remote from the pivotal attachment 23*c*. The cylinder strap 22 passes between the two portions of the adjuster 23 over the pivotal connection 23*c*. When the cylinder strap 22 is loose and freely movable within the adjuster 23, the two portions 23*a*, 23*b* of the adjuster are arranged at an angle to each other of less than 180° with each at a tangent to the surface curvature of an air cylinder located in the cylinder strap 22. In use, the cylinder strap 22 is pulled so that it is in contact about the air cylinder. Thereafter relative pivotal movement of the two portions 23*a*, 23*b* so that the angle between the two portions becomes ≥180°, in some embodiments greater than 180°, and the adjuster approximately follows the curvature of the air cylinder, causes a small length of the cylinder strap 22 to be pulled past the pivotal connection 23*c* further tightening the strap 22 about the cylinder. One of the two portions of the adjuster 23 includes, in combination with the other of the two portions or in combination with the pivotal attachment 23*c*, a catch which holds the relative position of the two portions 23*a*, 23*b* in their strap tightened position. The catch may comprise any conventional cam lock and again, like the waist buckle 14, the cam lock optionally includes a pair of opposed release buttons 23*d* to minimise the risk of the cylinder strap adjuster 23 being released by accident.

Alternatively, the cylinder strap 22 may be in two halves and include a buckle similar to the waist strap buckle 14 in combination with a parachute-type strap adjustment. In a further alternative the cylinder strap may include interengaging strips of hook and loop material such as Velcro™ material.

As mentioned earlier, the pneumatics mounting constitutes a first attachment member and the cylinder cradle 21 and the cylinder strap 22 constitute a second cylinder attachment member on the backplate and are attached to the backplate 11 at a position which is closer to the top edge of the backplate than the bottom edge. In some embodiments, the attachment position is approximately a third of the total length down from the top edge of the backplate which aligns approximately to the lower edge of the shoulder blades of the wearer. The separation of the first and second cylinder attachment members, corresponds to a distance greater than half the length of a conventional air cylinder. The position of the upper cylinder attachment member ensures that the air cylinder is prevented from projecting away from the back of the wearer when the wearer bends over. This reduces the risk of burning embers falling and catching between the air cylinder and the backplate. It also reduces the risk of the air cylinder snagging on obstacles. Furthermore, the relative positions of the two cylinder attachment members on the backplate 11 ensures that the air cylinder 2 is held close to the wearer's body at all times during use, irrespective of the movements of the wearer. Also, the combination of the rigidity of the backplate and the positions of the two cylinder attachment members ensures that, as the wearer moves, any momentum of the air cylinder relative to the wearer is minimized.

Also provided on the backplate 11 is an upper hose retaining strap 30*a* for holding the air hoses 4, which extend from the demand valve 3 to the mask 5 of the breathing apparatus, flat on the backplate 11. The hose retaining strap 30*a* is, in some embodiments, attached to the backplate 11 by means of hook and loop material such as Velcro™ ™ and is arranged to overlie and hold flat the sections of the two hoses 4 where they cross over each other. Hose clips may additionally be provided close to the upper ends of the shoulder straps to ensure that the hoses 4 line flat on the shoulder straps as well.

To keep the hoses flat against the backplate prior to their cross over at the upper section of the backplate, opposing edges of the cylinder cradle 21 are additionally provided with integral hose channels 30*b* which releaseably engage the hoses 4 and which are sized to provide an interference fit with respect to the hoses 4. Thus, the backplate includes hose holding means 30 (illustrated in detail in FIGS. 11*a* and 11*b*) which are fixedly attached to the backplate. As the backplate 11 is a single plate, no hose length adjustment is required between the first attachment member 24 and the hose retaining strap 30*a*. Thus, the combination of the hose channels 30*b* on the cylinder cradle 21 and the hose retaining strap 30*a* ensures that the hoses 4 lie flat on the backplate 11 and do not form loops which might catch on obstacles during use. Furthermore, both the hose channels 30*b* and the hose retaining strap 30*a* are adapted so that the hoses may be released manually without requiring any tools of any kind. Similarly, as mentioned earlier the first attachment member 24 enables the demand valve and pressure gauge to be manually released without the need for any tools. Thus, the carrying system described herein is adapted specifically to permit the breathing apparatus to be quickly and easily removed from the carrying system by hand i.e. without the need for any tools or other equipment.

On the inner surface of the backplate 11, namely the side of the backplate which faces towards the wearer, flame retardant padding 40 is provided. The padding is arranged in substantially parallel columns and is contoured to relieve pressure points and to follow the contours of a human back in at least one and optionally two dimensions. Hence, the padding 40 is arranged to have a central region of at least reduced thickness to accommodate the wearer's spine and optionally two columns substantially parallel to the central column which are again at least reduced in thickness to accommodate the muscles extending either side of the spine. To provide good quality padding with a high aspect ratio, the padding 40 is thermoformed onto the backplate 11, between the plate and the flame retardant material, and is optionally formed using a foamed polymer such as closed cell, cross-linked polyethylene. Thermoformed padding 40 may additionally be provided on the inner surfaces of the shoulder straps 12 and on the inner surface of the waist strap 13.

Figure 2:
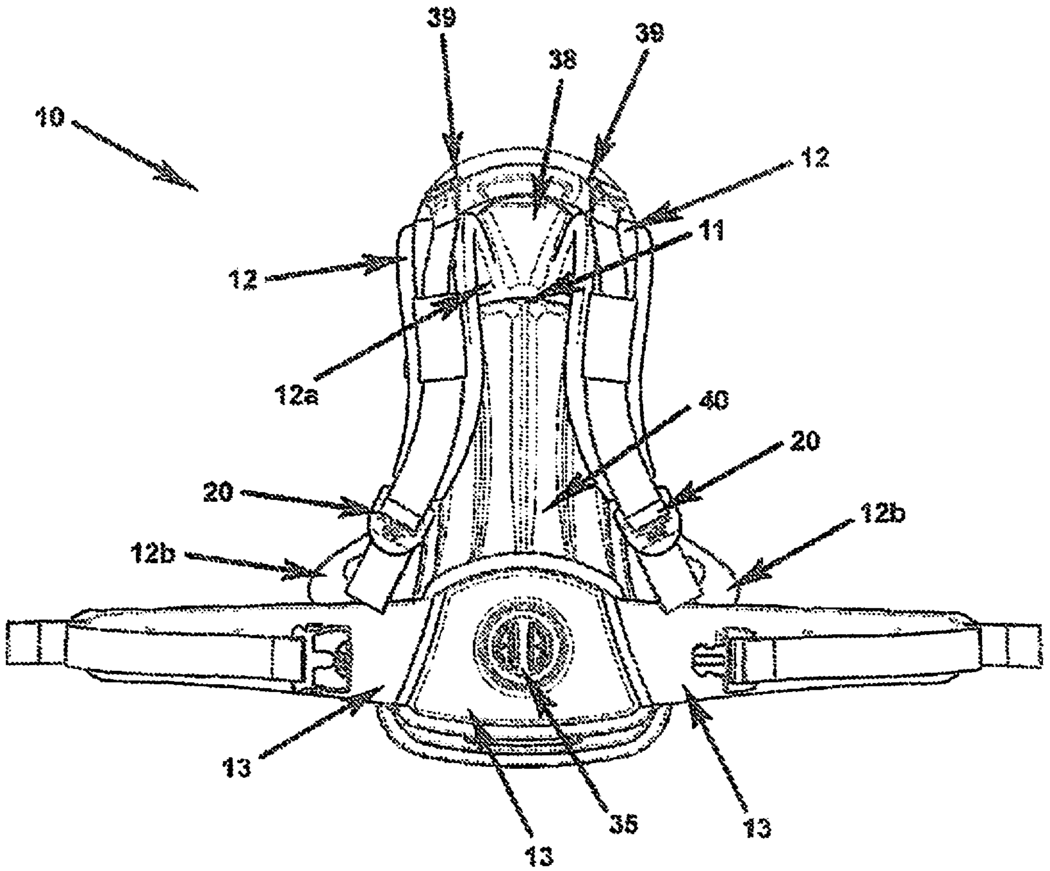
FIG. 2 is a diagrammatic illustration of the carrying system of FIG. 1 looking towards the inner, wearer-contacting side of the carrying system.

As shown in FIG. 2 the waist strap 13 is attached to the inner side of the backplate 11 and overlies a lower region of the backplate 11. Where the waist strap 13 overlies the backplate the width of the strap is greater than the strap width closer to the free ends 13*a* of the waist strap and in general the width of the waist strap tapers down towards its free ends 13*a*.

The waist strap 13 may be fixedly attached to the backplate 11 but, in some embodiments, the waist strap 13 is attached to the backplate 11 in a manner which permits the waist strap 13 to be selectively positioned in one of a plurality of separate different positions relative to the backplate 11 (three positions are illustrated in FIG. 6). In the adjustable configuration, the attachment of the waist strap 13 to the backplate 11 comprises an attachment guide 31 mounted on the inner surface of the backplate 11 and an attachment follower 32 which extends through and projects beyond the outer side of the waist strap 13 which faces away from the wearer, to engage with the attachment guide 31. As shown in FIG. 6 the attachment guide 31 comprises a guide plate which includes a pair of parallel guide slots 33 having opposed cut-outs 34 in three separate positions: at the top of each slot, at approximately the middle of each slot and at the bottom of each slot.

The attachment follower 32 comprises a handle 35 mounted in the inner side of the waist strap 13 connected to a pair of substantially parallel legs 36 which extend through the waist strap and project outwardly from the outer side of the waist strap. A U-shaped engaging member 37 is mounted on each of the free ends of the legs 36 and each engaging member 37 is arranged with their open end facing away from the other engaging member. A biasing member (not illustrated) is provided to bias the legs at a predetermined separation from each other. The handle 35 includes opposed slidable bars connected to the legs which are slidable against the action of the biasing member. A squeezing action by the user on the slidable bars of the handle 35, to reduce the spacing between the bars, causes an equivalent reduction in the separation of the two legs 36.

In use, the U-shaped engaging members 37 are positioned in their respective guide slots 33 of the attachment guide 31 with the U-shaped openings of the members 37 engaging the outer edge of their respective guide slot. The position of the waist strap 13 relative to the backplate 11 is therefore adjustable longitudinally (parallel to the width of the waist strap) through sliding movement of the engaging members 37 in their respective guide slots 33. However, when the engaging members 37 encounter opposing cut-outs 34 further sliding movement of the engaging members 37 is prevented by the edges of the cut-outs 34. Thus, each pair of cut-outs defines a fixed predetermined waist strap position relative to the backplate 11. Movement of the waist strap 13 to a different position requires a user to squeeze the slidable bars so as to move the engaging members 37 out of the cut-outs 34 and into the main guide slots. Thus, the waist strap is not adjustable longitudinally when the carrying system is being worn: longitudinal adjustment to accommodate the different back lengths of different wearers is performed prior to the carrying system being strapped tightly to the wearer. More importantly, as the waist strap 13 adopts a fixed position relative to the backplate 11 at each of its three (or more) predetermined positions, any load carried by the backplate 11 is constantly transmitted, via the attachment guide and the attachment follower, to the waist strap 13 and hence to the hips of the wearer. With the carrying system described herein, no or minimal load is transmitted to the shoulder straps.

Additionally, the waist strap 13 is capable of pivotal movement relative to the backplate 11. Such pivotal movement is useful to accommodate sideways or torsional movement of the wearer in the lumbar region. In order to enable pivotal movement of the waist strap 13, the waist strap 13 includes a recess in which the housing for the handle 35 is mounted. The housing of the handle 35 includes a siliconised ring (not shown) which functions as a bearing surface on which the handle 35 rests that permits rotational movement of the housing relative to the handle 35 housing. The extent of any rotation of the waist strap relative to the backplate 11 is restricted by means of one or more lugs that project from the surface of the handle and which engage in respective slots in the housing. The opposing ends of each slot define upper and lower rotation boundaries for the lugs.

Figure 10:
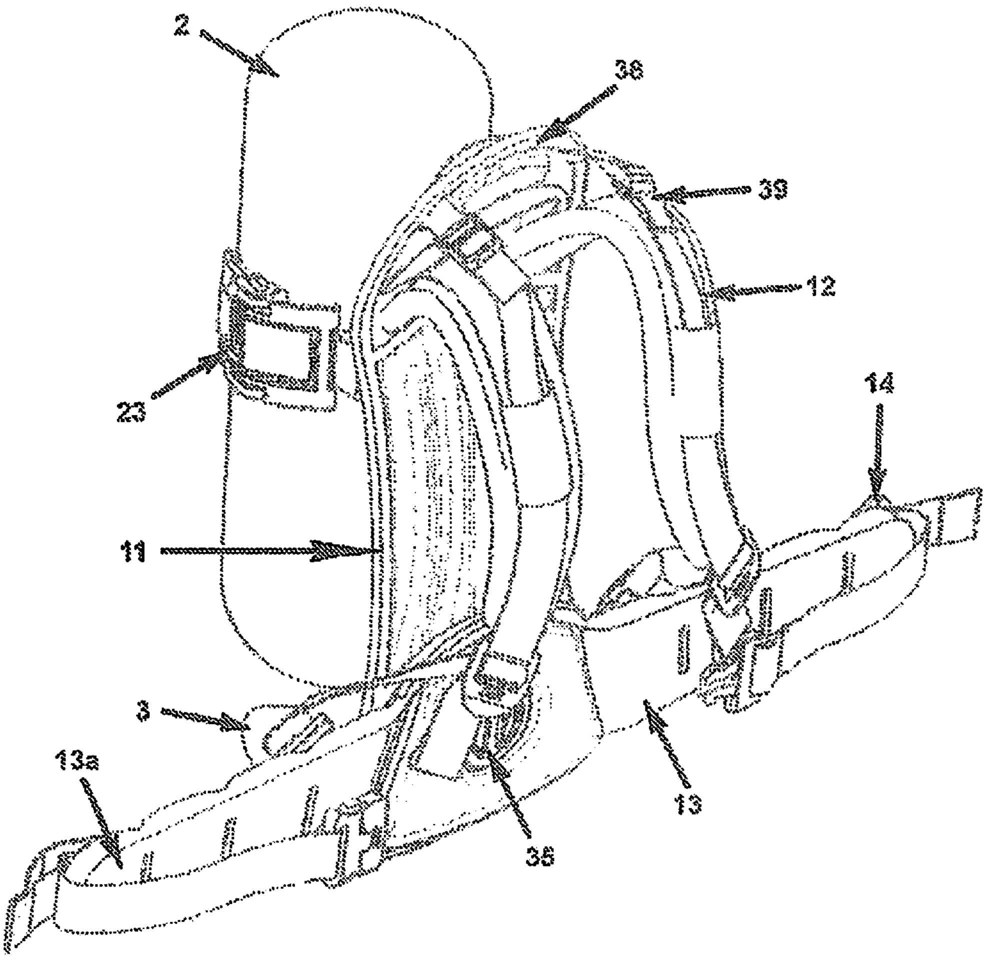
FIG. 10 is a perspective illustration of a carrying system in accordance with an embodiment of the present invention to which breathing apparatus is attached.
Figure 11A:
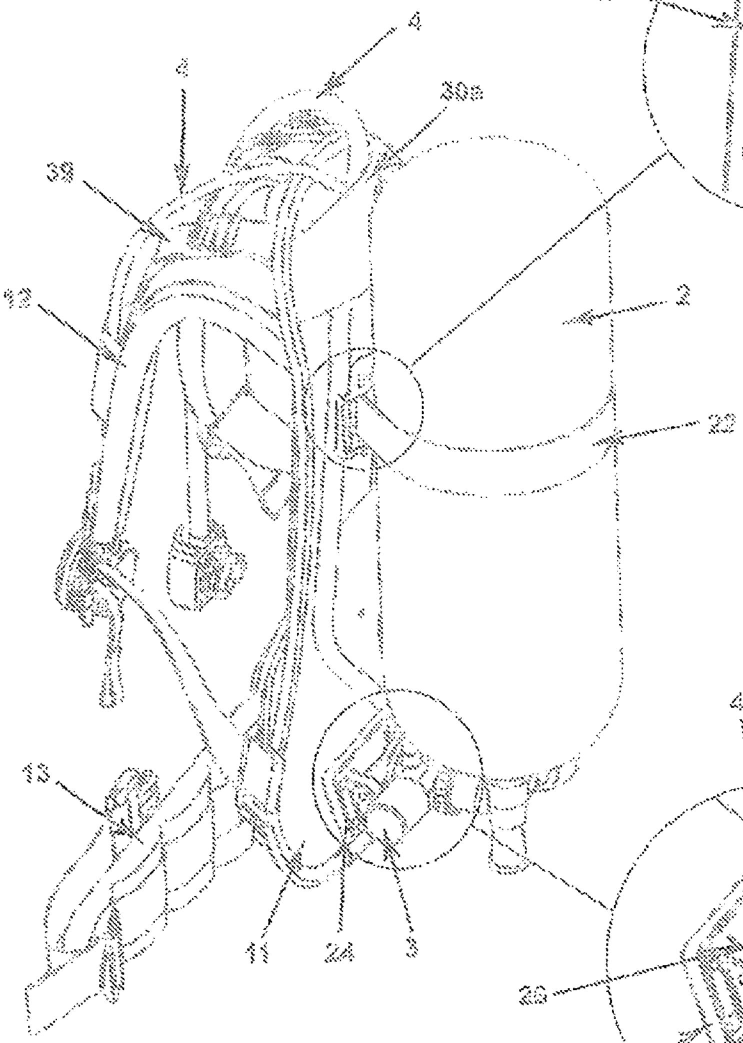
FIGS. 11*a*, 11*b* and 11*c* illustrate details of a breathing system attached to a carrying system in accordance with an embodiment the present invention.
Figure 11B:
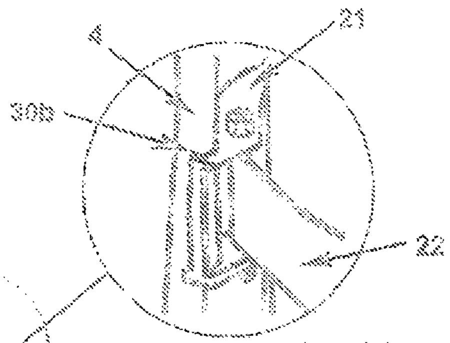
Figure 11C:
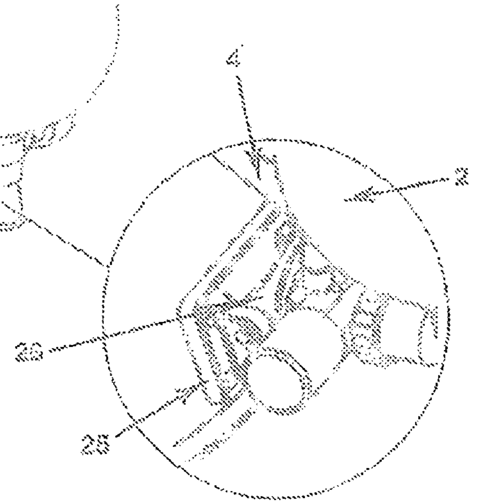

As shown in FIG. 10 particularly, an upper end portion of the backplate 11 functions as an upper guard 38. The upper guard 38 extends generally upwardly from the point of attachment of the shoulder straps 12 to the backplate 11 and has an arcuate upper edge. The distance of the arcuate upper edge from the point of attachment of the backplate with the shoulder straps is optionally equal to or greater than half the width of the backplate 11 at the point of attachment of the shoulder straps 12 to the backplate 11. As mentioned earlier, the backplate 11 is contoured and in the region of the upper guard 38, the backplate 11 curves away from the plane of the outer surface of the backplate at the point of attachment with the cylinder cradle 21.

A pair of tensioning straps 39 are attached at their upper ends, adjacent each other, to the upper edge of the upper guard 38 and at their lower ends to respective shoulder straps 12. The tensioning straps 39 are adjustable and are used to apply a tensioning force to the upper edge of the upper guard 38 so as to induce flexure of the upper guard 38 relative to the remainder of the backplate. By means of the tensioning straps 39 the upper guard 38 is urged to lie close to and to follow approximately the contours of the upper thoracic area of the wearer's back and/or at least part of the cervical area. Use of the tensioning straps 39 significantly reduces the risk of the upper edge of the backplate 11 catching on obstructions and also significantly reduces the risk of burning embers falling between the backplate 11 and the back of the wearer. The protective padding on the inner surface of the backplate is optionally extended to cover the upper guard region 38. Alternatively, separate padding may be provided in this region. Thus, the upper guard 38 provides protection for at least some of the cervical and/or upper thoracic vertebrae.

As mentioned earlier, the carrying system described above ensures that the weight of the carrying system and anything carried by the carrying system, such as air cylinders, is supported by the backplate which transmits the majority of the load to the waist strap 13 and thus to the wearer's hips, leaving the wearer's hands and arms free. Despite the backplate of the carrying system being a single plate and sufficiently rigid to minimise load momentum relative to the wearer of the carrying system, upper body movements of the wearer remain substantially unimpeded when wearing the carrying system due to the resiliency of the backplate and in particular its torsional resiliency. These load bearing characteristics of the carrying system in combination with the contoured backplate incorporating contoured thermoformed padding provides superior wearer comfort and offers significant reductions in wearer fatigue.

The combination of the resilient guard and the tensioning straps minimises any snagging risks as well as minimising the risk of burning embers penetrating any space between the back of the wearer and the backplate. The guard also provides further impact protection specifically to at least some cervical and/or upper thoracic vertebrae.

Also, the carrying system has been developed to minimise snagging risks for example by ensuring that the air cylinder is held close to the wearer's body and that the air hoses of the breathing apparatus lie flat and smooth against the backplate. Further safety features include locking strap buckles with opposing pairs of release buttons to minimise the risk of the straps being released accidentally.

The carrying system additionally offers the significant advantage of being suitable for conventional cleaning in a standard washing machine. This is possible as a result of the first attachment member providing a simple, quick and manually operable mechanism for detaching the air cylinder, the demand valve and the pressure gauge from the carrying system and as a result of the air hoses being manually removable from permanent fittings on the backplate. Thus all parts of the breathing apparatus can be removed from the carrying system manually and quickly without requiring the use of any tools or other specialised equipment.

All of the features of the carrying system described above, in combination, provide a carrying system for use, for example, by fire fighters which greatly increases comfort, reduces wearer fatigue and which offers a significant improvement in terms of wearer safety.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the subject matter described and/or illustrated herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The invention claimed is:

1. A carrying system for use with breathing apparatus, the carrying system comprising:

a backplate configured to receive a breathing apparatus mounted thereto, the backplate comprising a unitary, one-piece plate formed of a plastic material, the plate having a predetermined shape including an upper end region and a lower end region, the plate having an inner side and an opposite outer side, the inner side facing a user when the carrying system is worn by the user, the plate being configured to provide impact protection to the user during use by at least one of absorbing or dispersing impact forces, the plate being configured to deform resiliently in response to external forces imposed by at least one of bending or twisting of the user during use and return substantially to its predetermined shape when not subjected to an external force;

an attachment member mounted on the outer side of the plate, the attachment member configured to releasably mount a breathing apparatus that includes an air cylinder along the outer side such that the plate is disposed between the breathing apparatus and the user;

two shoulder straps attached to the plate of the backplate at the upper end region; and a waist strap attached to the plate of the backplate at the lower end region, the waist strap including an attachment segment thereof, the attachment segment being attached to the plate and overlying the lower end region of the plate, the waist strap and the shoulder straps configured to hold the backplate on a back of the user when the carrying system is worn by the user such that when the user's back undergoes a twisting movement, the waist strap and the shoulder straps impose a torsional force on the plate causing the plate to deform torsionally.

2. The carrying system of claim 1, wherein the plate of the backplate has a mid-section extending between the upper end region and the lower end region, the upper and lower end regions being wider than the mid-section.

3. The carrying system of claim 1, wherein the shoulder straps are attached to the plate at first points of attachment, the backplate comprising an upper guard region extending between the first points of attachment and an upper edge of the backplate, the carrying system further comprising two tensioning straps attached to and extending between the upper guard region and the shoulder straps, the tensioning straps attached to the upper guard region at second points of attachment spaced apart from the first points of attachment of the shoulder straps to the plate, the upper guard region configured to flex relative to a remainder of the backplate when tension is applied to the tensioning straps so as to substantially overlie and protect at least one of the cervical area or the upper thoracic area of the user.

4. The carrying system of claim 1, wherein the backplate further comprises one or more areas of thermoformed padding.

5. The carrying system of claim 1, wherein the waist strap is pivotally attached to the plate of the backplate to permit relative pivotal movement between the waist strap and the plate.

6. The carrying system of claim 1, wherein the backplate extends along a central longitudinal axis, the plate being configured to twist about the central longitudinal axis in response to the twisting movement of the user's back.

7. The carrying system of claim 1, wherein the upper end region of the plate aligns approximately with an upper thoracic region of the user's back and the lower end region aligns approximately with a lumbar region of the user's back.

8. The carrying system of claim 1, wherein the plate of the backplate is the only plate of the backplate.

9. The carrying system of claim 1, wherein at least one of the inner side or the outer side of the plate is covered in a flame retardant material.

10. The carrying system of claim 1, wherein the shoulder straps and the waist strap are directly attached to the plate of the backplate.

11. The carrying system of claim 1, wherein the plate of the backplate extends a length between a top end and a bottom end, the top end of the plate disposed above the waist strap along the length of the plate, the bottom end of the plate disposed below the waist strap along the length of the plate.

12. The carrying system of claim 1, wherein the attachment segment of the waist strap that overlies the lower end region of the plate is attached to the inner side of the plate.

13. A carrying system for use with breathing apparatus, the carrying system comprising:

a backplate comprising a unitary, one-piece plate, the plate including an upper end region and a lower end region;

two shoulder straps attached to the plate of the backplate at the upper end region; and a waist strap attached to the plate of the backplate at the lower end region, the waist strap including an attachment segment thereof, the attachment segment being attached to the plate and overlying the lower end region of the plate, the waist strap and the shoulder straps configured to hold the backplate on a back of a user when the carrying system is worn by the user such that when the user's back undergoes a twisting movement, the waist strap and the shoulder straps impose a torsional force on the plate of the backplate causing the plate to deform torsionally, the backplate further comprising:

a first attachment member mounted on the plate configured to releasably mount a breathing apparatus to the backplate, the first attachment member being configured to releasably attach to a connecting part of the breathing apparatus that connects an air cylinder to one or more air supply hoses; and a locking element configured to be attached to the connecting part of the breathing apparatus, the locking element being rotatable relative to the first attachment member between a locked position and an unlocked position, the connecting part and the first attachment member being locked together when the locking element is in the locked position, the connecting part and the first attachment member being releasable from each other when the locking element is in the unlocked position, wherein the first attachment member is manually releasably attachable to and from the connecting part of the breathing apparatus by the user without the use of a tool.

14. The carrying system of claim 13, wherein the first attachment member comprises an aperture configured to receive the locking element, the aperture being shaped to permit the locking element to rotate within the aperture between the unlocked and locked positions.

15. The carrying system of claim 13, wherein the locking element comprises a shoulder that is configured to engage an edge of the first attachment member when the locking element is in the locked position, the shoulder being configured to disengage the edge when the locking element is in the unlocked position.

16. The carrying system of claim 13, wherein the locking element comprises a shoulder that is configured to engage an edge of an aperture of the first attachment member when the locking element is in the locked position, a pressure of air flowing through the connecting part acts on at least one of the shoulder, another shoulder, or a flange of the locking element to rotationally fix the locking element in the locked position.

17. The carrying system of claim 13, wherein the backplate further comprises a second attachment member mounted on the plate of the backplate, the second attachment member comprising a cylinder supporting surface and an adjustable flexible strap for encircling the air cylinder of the breathing apparatus, the cylinder supporting surface and the flexible strap forming a continuous loop having a manually adjustable diameter to conform to the diameter of the air cylinder.

18. The carrying system of claim 17, wherein the flexible strap includes a strap lock for locking the strap at a chosen strap loop diameter, the strap lock comprising a pair of pivotally connected strap holding members wherein the pivotal connection of the pair of strap holding members includes a locking mechanism for locking the relative position of the pair of strap holding members, the locking mechanism further includes a pair of opposing release buttons for manual release of the locking mechanism.

19. The carrying system of claim 17, wherein the second attachment member further includes one or more hose channels for releasably engaging one or more air supply hoses of the breathing apparatus, the hose channels being configured to provide an interference fit for the air supply hoses, whereby a user may engage and disengage the one or more air supply hoses to and from the hose channels without the use of a tool.

20. The carrying system of claim 17, wherein the first and second attachment members are separated by a distance corresponding to over half the length of the air cylinder of the breathing apparatus.

21. A carrying system for use with breathing apparatus, the carrying system comprising:

a backplate comprising a unitary, one-piece plate, the plate including an upper end region and a lower end region;

two shoulder straps attached to the plate of the backplate at the upper end region; and a waist strap attached to the plate of the backplate at the lower end region, the waist strap including an attachment segment thereof, the attachment segment being attached to the plate and overlying the lower end region of the plate, the waist strap and the shoulder straps configured to hold the backplate on a back of a user when the carrying system is worn by the user such that when the user's back undergoes a twisting movement, the waist strap and the shoulder straps impose a torsional force on the plate causing the plate to deform torsionally, the backplate further comprising:

a first attachment member mounted on the plate configured to releasably mount a breathing apparatus to the backplate, the first attachment member being configured to releasably attach to a connecting part of the breathing apparatus that connects an air cylinder to one or more air supply hoses; and a locking element configured to be attached to the connecting part of the breathing apparatus, the locking element having a locked position and an unlocked position, the connecting part and the first attachment member being locked together when the locking element is in the locked position, the connecting part and the first attachment member being releasable from each other when the locking element is in the unlocked position, wherein a pressure of air flowing through the connecting part holds the locking element in the locked position during use of the breathing apparatus by the user, and wherein the first attachment member is manually releasably attachable to and from the connecting part of the breathing apparatus by the user without the use of a tool.

22. The carrying system of claim 21, wherein the locking element is rotatable relative to the first attachment member between the locked and unlocked positions.

23. The carrying system of claim 21, wherein the locking element comprises a shoulder and the first attachment member defines an aperture that is configured to receive the locking element therein, the shoulder of the locking element being configured to engage an edge of the aperture when the locking element is in the locked position within the aperture, the shoulder of the locking element being configured to disengage the edge of the aperture when the locking element is in the unlocked position within the aperture.

* * * * *